(12) United States Patent
Crossgrove et al.

(10) Patent No.: US 10,413,333 B2
(45) Date of Patent: Sep. 17, 2019

(54) SYSTEM AND METHOD FOR SPINAL FIXATION VIA A TRANS-FACET PEDICLE SCREW ASSEMBLY

(71) Applicant: SPINEFRONTIER, INC, Malden, MA (US)

(72) Inventors: Jeremy Crossgrove, Brookline, MA (US); Michael Emery, Windham, NH (US); Jacob Lubinski, Beverly, MA (US); Lin Yin, Brighton, MA (US); Kingsley R. Chin, Wilton Manors, FL (US)

(73) Assignee: SPINEFRONTIER, INC, Malden, MA (US)

( * ) Notice: Subject to any disclaimer, the term of this patent is extended or adjusted under 35 U.S.C. 154(b) by 29 days.

(21) Appl. No.: 15/724,827

(22) Filed: Oct. 4, 2017

(65) Prior Publication Data
US 2018/0092670 A1 Apr. 5, 2018

Related U.S. Application Data

(60) Provisional application No. 62/404,342, filed on Oct. 5, 2016.

(51) Int. Cl.
*A61B 17/70* (2006.01)
*A61B 17/88* (2006.01)
(Continued)

(52) U.S. Cl.
CPC ...... *A61B 17/7064* (2013.01); *A61B 17/7032* (2013.01); *A61B 17/7037* (2013.01);
(Continued)

(58) Field of Classification Search
CPC ............ A61B 17/7064; A61B 17/7032; A61B 17/7037; A61B 17/8665; A61B 17/7002;
(Continued)

(56) References Cited

U.S. PATENT DOCUMENTS 8,562,649 B2 * 10/2013 Triplett .............. A61B 17/1757
606/247
2006/0084981 A1 * 4/2006 Shluzas .............. A61B 17/7037
606/328

(Continued)

*Primary Examiner* — Pedro Philogene
*Assistant Examiner* — David C Comstock
(74) *Attorney, Agent, or Firm* — AKC Patents, LLC; Aliki K. Collins

(57) ABSTRACT

A spinal fixation device includes a bone screw, a tulip-shaped seat, a rod seat, and a washer. The bone screw comprises a spherical head and a threaded elongated body extending along a first direction. The tulip-shaped seat comprises a bottom portion that has a through-opening shaped and dimensioned to receive the bone screw so that an inner surface of the bottom portion engages the spherical head of the bone screw and prevents the bone screw from passing entirely through the through-opening, while the spherical head remains polyaxially rotatable within the bottom portion of the tulip-shaped seat. The rod seat sits within and engages the inner surface of the tulip-shaped seat and the rod seat comprises a semispherical bottom that is shaped and dimensioned to engage the spherical head of the bone screw while the spherical head remains polyaxially rotatable within the bottom portion of the tulip-shaped seat. The washer is ring-shaped and comprises a through-opening shaped and dimensioned to receive the threaded elongated body of the bone screw and an upper portion shaped and dimensioned to snappably-engage an outer surface of the tulip-shaped seat.

14 Claims, 13 Drawing Sheets

(51) Int. Cl.
  *A61B 17/86*  (2006.01)
  *A61B 17/56*  (2006.01)
(52) U.S. Cl.
  CPC ...... *A61B 17/8665* (2013.01); *A61B 17/7002* (2013.01); *A61B 17/8685* (2013.01); *A61B 17/8695* (2013.01); *A61B 2017/564* (2013.01)
(58) Field of Classification Search
  CPC ............ A61B 17/8685; A61B 17/8695; A61B 2017/564
  USPC ................ 606/247, 264–267, 279, 308, 328
  See application file for complete search history.

(56) References Cited

U.S. PATENT DOCUMENTS

| | | | | |
|---|---|---|---|---|
| 2011/0288588 | A1* | 11/2011 | Chin | A61B 17/7064 606/247 |
| 2012/0116454 | A1* | 5/2012 | Edidin | A61B 17/1757 606/247 |
| 2014/0142634 | A1* | 5/2014 | Schlaepfer | A61B 17/704 606/278 |
| 2014/0288601 | A1* | 9/2014 | Baynham | A61B 17/7064 606/247 |
| 2015/0201972 | A1* | 7/2015 | Doubler | A61B 17/7002 606/266 |
| 2017/0049481 | A1* | 2/2017 | Faulhaber | A61B 17/7032 |

* cited by examiner

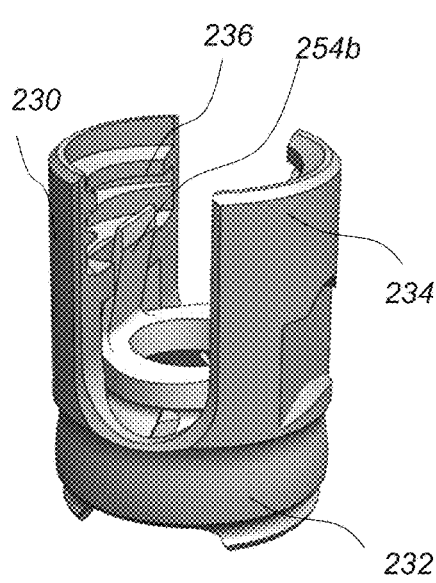
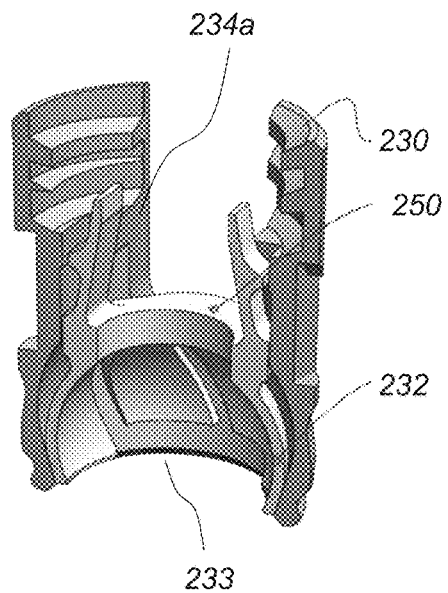
FIG. 9A   FIG. 9B
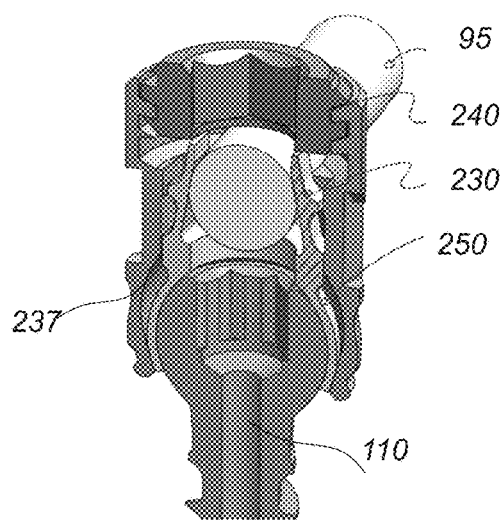
FIG. 9C

SYSTEM AND METHOD FOR SPINAL FIXATION VIA A TRANS-FACET PEDICLE SCREW ASSEMBLY

CROSS REFERENCE TO RELATED CO-PENDING APPLICATIONS

This application claims the benefit of U.S. provisional application Ser. No. 62/404,342 filed Oct. 5, 2016 and entitled "SYSTEM AND METHOD FOR SPINAL FIXATION VIA A TRANS-FACET PEDICLE SCREW ASSEMBLY", the contents of which are expressly incorporated herein by reference.

FIELD OF THE INVENTION

The present invention relates to a system and method for spinal fixation and in particular to spinal fixation via a trans-facet pedicle screw assembly.

BACKGROUND OF THE INVENTION

Disorders of the spine occur when one or more of the individual vertebras and/or the inter-vertebral discs become abnormal either as a result of disease or injury. In these pathologic circumstances, fusion of adjacent vertebral segments may be tried to restore the function of the spine to normal, achieve stability, protect the neural structures, or to relieve the patient of discomfort.

Several spinal fixation systems exist for stabilizing the spine so that bony fusion is achieved. The majority of these fixation systems utilize fixation elements such as rods wires or plates that attach to screws threaded into the vertebral bodies or the pedicles. In particular, spinal fixation systems that attach to the pedicles (i.e., trans-pedicular) are very popular due to their stability. However, trans-pedicular fixation systems and methods require excessive muscle dissection and have been associated with harmful side effects including muscle and nerve damage in the spinal areas and increased infections, among others.

Because the outer surface of the vertebral body is typically non-planar and the structure of the vertebras is relatively complex, it is important that the fixation elements (e.g., rods, plates, wires, staples and/or screws) are properly aligned when they are inserted into the vertebras. Improper alignment may result in improper or unstable placement of the fixation element and/or disengagement of the fixation element. However, achieving and maintaining accurate positioning and guidance of these fixation elements has proven to be quite difficult in practice. Such positioning difficulties are further complicated by the fact that the alignment angle for a fixation device through one vertebral body or pair of vertebral bodies will be unique to that individual due to individual differences in the spinal curvature and anatomies.

Accordingly, there is a need for alternative fixation systems and methods that are easy to align and alleviate the above mentioned complications.

SUMMARY OF THE INVENTION

The present invention relates to a system and method for spinal fixation and in particular spinal fixation via a trans-facet pedicle screw assembly.

In general, in one aspect, the invention features a spinal fixation device including a bone screw, a tulip-shaped seat, a rod seat, and a washer. The bone screw comprises a spherical head and a threaded elongated body extending along a first direction. The tulip-shaped seat comprises a bottom portion that has a through-opening shaped and dimensioned to receive the bone screw so that an inner surface of the bottom portion engages the spherical head of the bone screw and prevents the bone screw from passing entirely through the through-opening, while the spherical head remains polyaxially rotatable within the bottom portion of the tulip-shaped seat. The rod seat sits within and engages the inner surface of the tulip-shaped seat and the rod seat comprises a semispherical bottom that is shaped and dimensioned to engage the spherical head of the bone screw while the spherical head remains polyaxially rotatable within the bottom portion of the tulip-shaped seat. The washer is ring-shaped and comprises a through-opening shaped and dimensioned to receive the threaded elongated body of the bone screw and an upper portion shaped and dimensioned to snappably-engage an outer surface of the tulip-shaped seat.

Implementations of this aspect of the invention may include one or more of the following features. The rod seat further comprises a top portion with a semi-circular horizontal cut-out and is shaped and dimensioned to receive a rod extending along a second direction. The rod seat rotationally engages the inner surface of the tulip-shaped seat and further comprises a circular protrusion around a portion of an outer surface and the circular protrusion engages a groove formed on the inner surface of the tulip-shaped seat and locks the position of the rod seat within the tulip-shaped seat so that the semi-circular horizontal cut-out of the rod seat is aligned with a semi-circular cut-out of the tulip-shaped seat. The device further includes a cap shaped and dimensioned to engage inner threads formed on an inner surface of a top portion of the tulip-shaped seat and to secure a rod within the rod seat. The device further includes a snap-ring and an inner surface of the top portion of the washer comprises a groove that is dimensioned to receive the snap-ring and to snappably secure the washer onto the outer surface of the tulip-shaped seat. The washer further includes protrusions extending downward from a bottom portion of the washer. The spherical head of the bone screw comprises a hexagonal top opening and the hexagonal top opening extends into a cylindrical opening of the elongated body of the bone screw and the cylindrical opening extends along the first direction from the elongated body's top end to its bottom end. The spinal fixation element passes through and connects opposing facets of two adjacent vertebras and is anchored along a trajectory that leads into a vertebral body of one of the adjacent vertebras.

In general in another aspect the invention features a spinal fixation device including a bone screw, a tulip-shaped seat, and rod seat. The bone screw comprises a spherical head and a threaded elongated body extending along a first direction. The tulip-shaped seat comprises a through-opening shaped and dimensioned to receive the rod seat. The rod seat sits within and snappably engages an inner surface of the tulip-shaped seat and the rod seat comprises a semispherical bottom that is shaped and dimensioned to snappably engage the spherical head of the bone screw. The rod seat comprises two upward extending tabs that are dimensioned to receive a rod extending along a second direction and the bottom of the rod seat comprises flexible segments that snappably engage the spherical head of the bone screw.

In general in another aspect the invention features a spinal fixation system including a spinal fixation element extending along a first direction, and a rod supported onto the spinal fixation element and extending along a second direction. The spinal fixation element comprises a bone screw, a tulip-shaped seat, a rod seat, a cap, and a washer. The bone screw comprises a spherical head and a threaded elongated body extending along a first direction. The tulip-shaped seat comprises a bottom portion that has a through-opening shaped and dimensioned to receive the bone screw so that an inner surface of the bottom portion engages the spherical head of the bone screw and prevents the bone screw from passing entirely through the through-opening, while the spherical head remains polyaxially rotatable within the bottom portion of the tulip-shaped seat. The rod seat sits within and engages the inner surface of the tulip-shaped seat and the rod seat comprises a semispherical bottom that is shaped and dimensioned to engage the spherical head of the bone screw while the spherical head remains polyaxially rotatable within the bottom portion of the tulip-shaped seat, and the rod seat further comprises a top portion with a semi-circular horizontal cut-out that is shaped and dimensioned to receive the rod extending along the second direction. The washer is ring-shaped and comprises a through-opening shaped and dimensioned to receive the threaded elongated body of the bone screw and an upper portion shaped and dimensioned to snappably-engage an outer surface of the tulip-shaped seat. The spinal fixation element passes through and connects opposing facets of two adjacent vertebras and is anchored along a trajectory that leads into a vertebral body of one of the adjacent vertebras.

In general in another aspect the invention features a trans-facet spinal fixation system including first and second trans-facet spinal fixation elements and a rod. The first trans-facet spinal fixation element passes through and connects a superior facet of a first vertebra to an opposing inferior facet of an adjacent second vertebra and is anchored along a trajectory that leads into a vertebral body of the first vertebra. The second trans-facet spinal fixation element passes through and connects a superior facet of a third vertebra to an opposing inferior facet of an adjacent fourth vertebra and is anchored along a trajectory that leads into a vertebral body of the third vertebra. The rod is supported onto the first and second trans-facet spinal fixation elements.

Implementations of this aspect of the invention may include one or more of the following features. Each of the trans-facet spinal fixation elements comprises a bone screw, a tulip-shaped seat, a rod seat, and a washer, and the bone screw comprises a spherical head and a threaded elongated body, the tulip-shaped seat comprises a bottom portion that has a through-opening shaped and dimensioned to receive the bone screw so that an inner surface of the bottom portion engages the spherical head of the bone screw and prevents the bone screw from passing entirely through the through-opening, while the spherical head remains polyaxially rotatable within the bottom portion of the tulip-shaped seat, the rod seat sits within and engages the inner surface of the tulip-shaped seat and the rod seat comprises a semispherical bottom that is shaped and dimensioned to engage the spherical head of the bone screw while the spherical head remains polyaxially rotatable within the bottom portion of the tulip-shaped seat, wherein the rod seat further comprises a top portion with a semi-circular horizontal cut-out and is shaped and dimensioned to receive the rod, and wherein the washer is ring-shaped and comprises a through-opening shaped and dimensioned to receive the threaded elongated body of the bone screw and an upper portion shaped and dimensioned to snappably-engage an outer surface of the tulip-shaped seat. Each of the trans-facet spinal fixation elements comprises a bone screw, a tulip-shaped seat, and a rod seat and wherein the bone screw comprises a spherical head and a threaded elongated body extending along a first direction, wherein the tulip-shaped seat comprises a through-opening shaped and dimensioned to receive the rod seat, and wherein the rod seat sits within and snappably engages an inner surface of the tulip-shaped seat and wherein the rod seat comprises a semispherical bottom that is shaped and dimensioned to snappably engage the spherical head of the bone screw.

In general in another aspect the invention features a spinal fixation system including a trans-facet spinal fixation element, a trans-pedicle spinal fixation element, and a rod. The trans-facet spinal fixation element passes through and connects a superior facet of a first vertebra to an opposing inferior facet of an adjacent second vertebra and is anchored along a trajectory that leads into a vertebral body of the first vertebra. The trans-pedicle spinal fixation element is anchored into a pedicle of a third vertebra and the rod is supported onto the trans-facet spinal fixation element and the trans-pedicle spinal fixation element.

In general in another aspect the invention features a trans-facet spinal fixation method including the following. First, inserting a first trans-facet spinal fixation element through a superior facet of a first vertebra, and through an opposing inferior facet of an adjacent second vertebra and anchoring the first trans-facet spinal fixation element along a trajectory that leads into a vertebral body of the first vertebra. Next, inserting a second trans-facet spinal fixation element through a superior facet of a third vertebra, and through an opposing inferior facet of an adjacent fourth vertebra and anchoring the second trans-facet spinal fixation element along a trajectory that leads into a vertebral body of the third vertebra. Next, inserting and supporting a rod onto the first and second trans-facet spinal fixation elements.

In general in another aspect the invention features a spinal fixation method including the following. First, inserting a trans-facet spinal fixation element through a superior facet of a first vertebra, and through an opposing inferior facet of an adjacent second vertebra and anchoring the first trans-facet spinal fixation element along a trajectory that leads into a vertebral body of the first vertebra. Next, inserting and anchoring a trans-pedicle spinal fixation element into a pedicle of a third vertebra. Next, inserting and supporting a rod onto the trans-facet spinal fixation element and the trans-pedicle spinal fixation element.

Among the advantages of this invention may be one or more of the following. The spinal fixation assembly of the present invention fixates a superior vertebra to an inferior vertebra via a single facet fixation element on each side of the spinal column. Alignment of the single facet fixation element is easier than aligning two fixation elements that would have been required by the prior art pedicle screw fixation systems. This reduction in the number of fixation elements also allows for a reduction of the incision size and the potential complications associated with them.

BRIEF DESCRIPTION OF THE DRAWINGS

Referring to the figures, wherein like numerals represent like parts throughout the several views:

FIG. 9A depicts a perspective view of the upper portion of the spinal fixation assembly of FIG. 8;

FIG. 9B depicts a cross-sectional view of the upper portion of the spinal fixation assembly of FIG. 8; and FIG. 9C depicts a cross-sectional view of the assembled upper portion of the spinal fixation assembly of FIG. 8.

DETAILED DESCRIPTION OF THE INVENTION

The present invention relates to a system and method for spinal fixation and in particular spinal fixation via a trans-facet pedicle screw assembly.

Figure 1A:
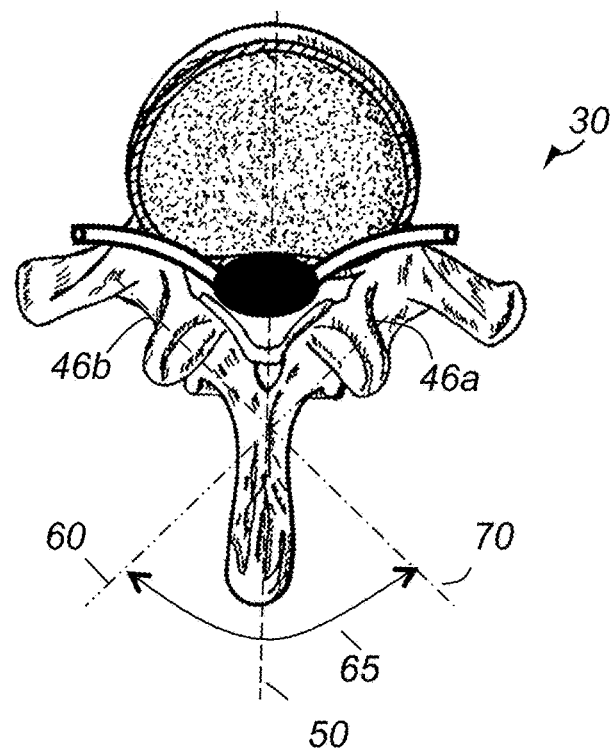
FIG. 1A depicts an axial cross-sectional view of a lumbar vertebra and illustrates placement directions of two facet screws for securing two facet joints.
Figure 1B:
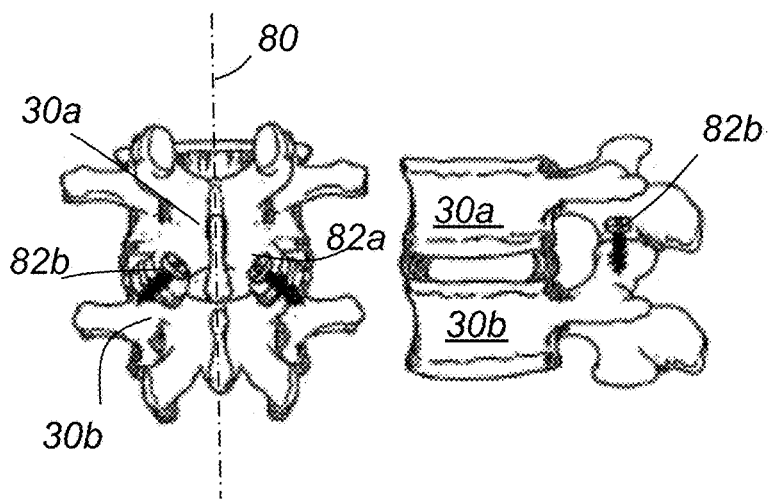
FIG. 1B depicts a prior art spinal fixation system including two facet screws mounted on two adjacent vertebras bilaterally symmetrically to the spinal midline 80.

Referring to FIG. 1A and FIG. 1B, a prior art trans-facet fixation system includes spinal fixation elements 82a, 82b that are used to secure together first and second facet joints 46a, 46b. The spinal fixation elements 82a, 82b are inserted along the directions 60, 70, respectively. Directions 60, 70 form an angle 65 between them. In most cases, directions 60, 70 are symmetrically positioned to the left and right of the spinal midline 80, which is perpendicular to the dichotome 50 of angle 65. In this example, fixation elements 82a, 82b are facet screws and are placed in a trans-facet way for connecting adjacent vertebras 30a, 30b. In other examples, fixation elements 82a, 82b, may be staples, wires, or pins, and they may connect adjacent or non-adjacent vertebras via trans-facet, trans-laminar, trans-facet-pedicular, trans-pedicular, or through any other vertebral location.

Figure 2A:
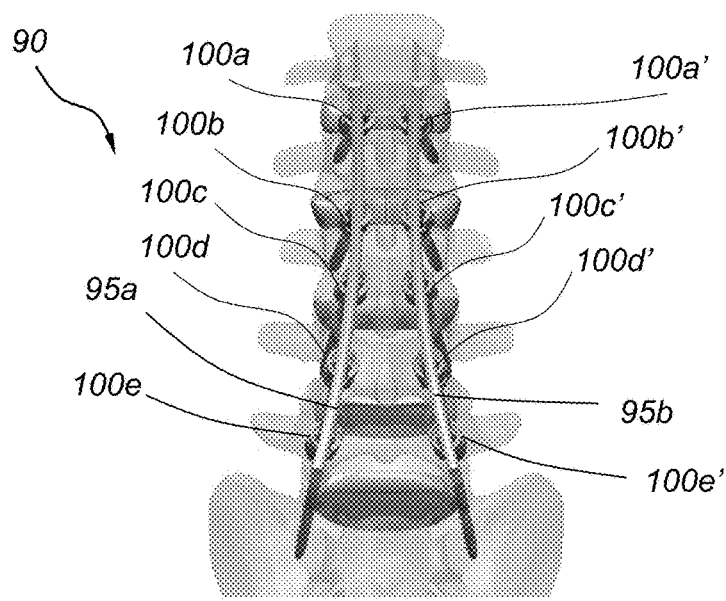
FIG. 2A depicts a posterior view of a spinal fixation system according to this invention.
Figure 2B:
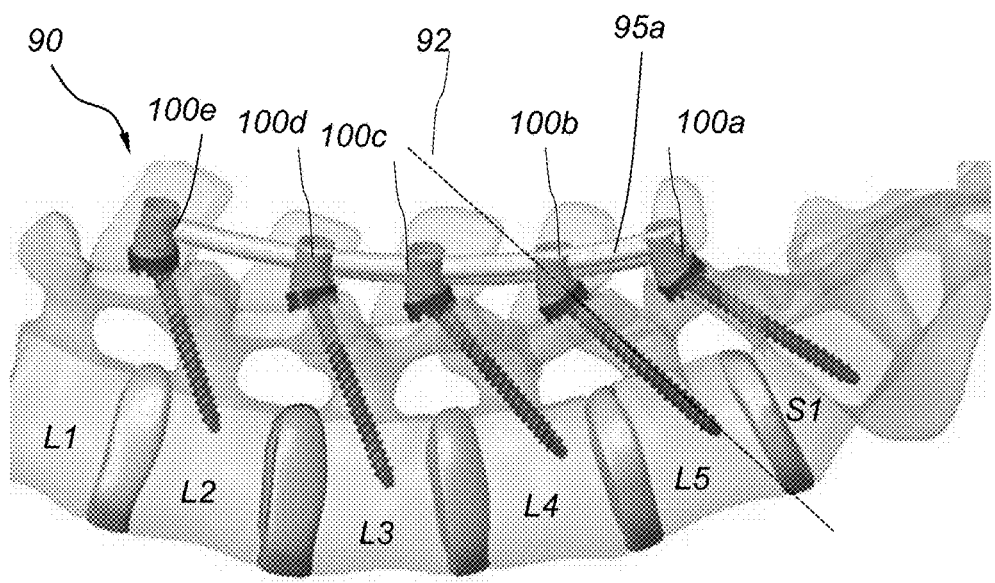
FIG. 2B depicts a side view of a spinal fixation system according to this invention.
Figure 3A:
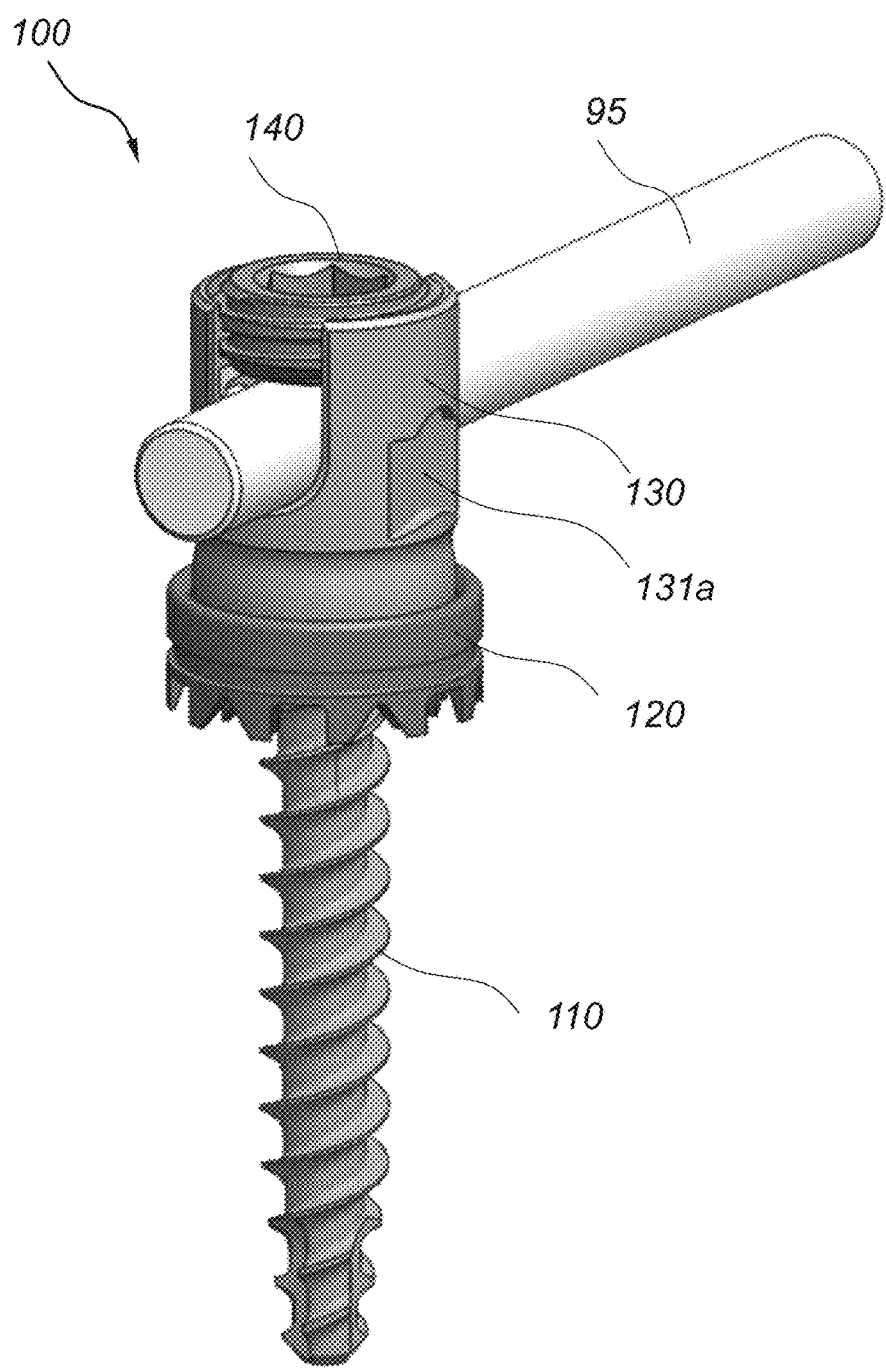
FIG. 3A depicts a trans-facet spinal fixation assembly according to this invention.
Figure 3B:
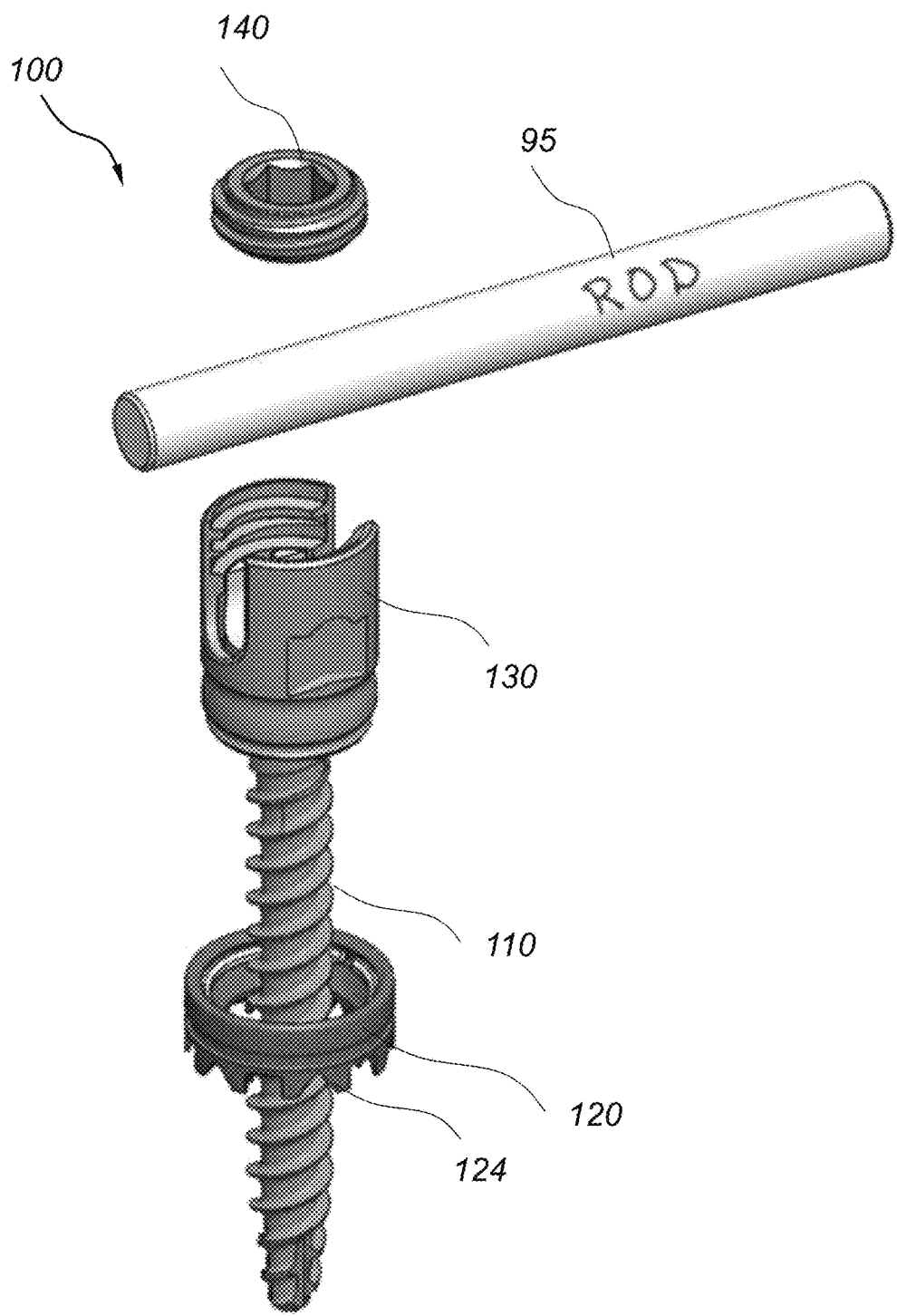
FIG. 3B depicts a partially exploded view of the spinal fixation assembly of FIG. 3A.
Figure 4A:
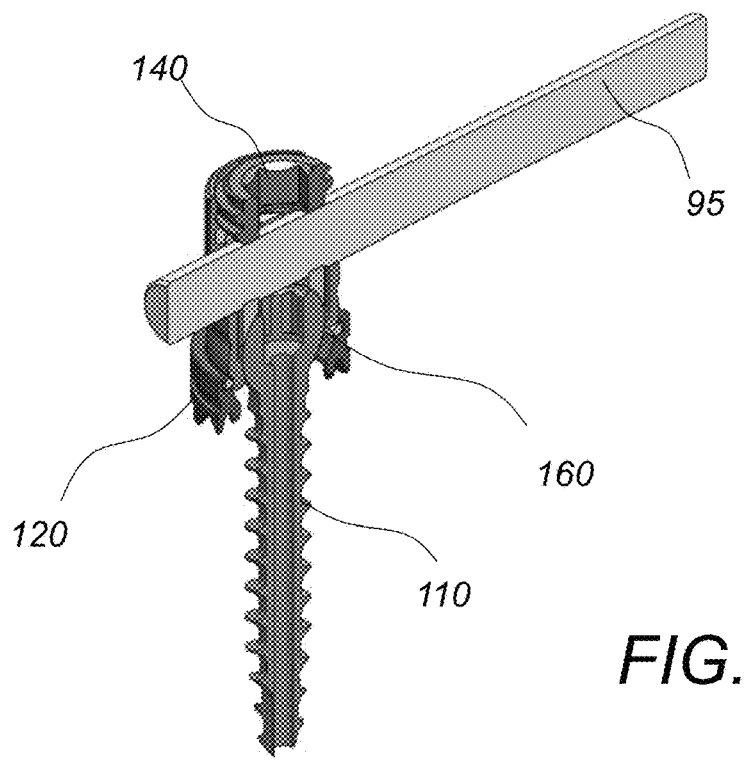
FIG. 4A depicts a cross-sectional view of the spinal fixation assembly of FIG. 3A.
Figure 4B:
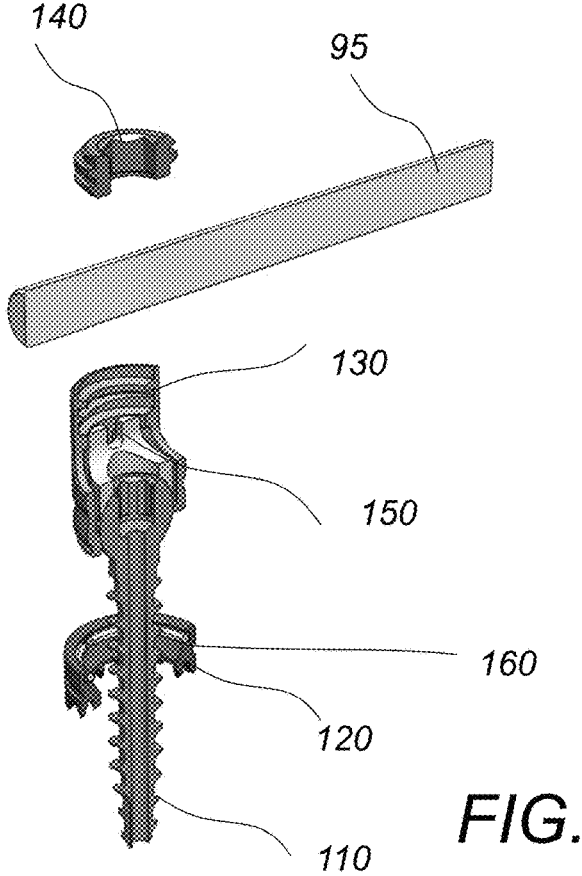
FIG. 4B depicts a cross-sectional view of the partially exploded spinal fixation assembly of FIG. 3B.
Figure 5A:
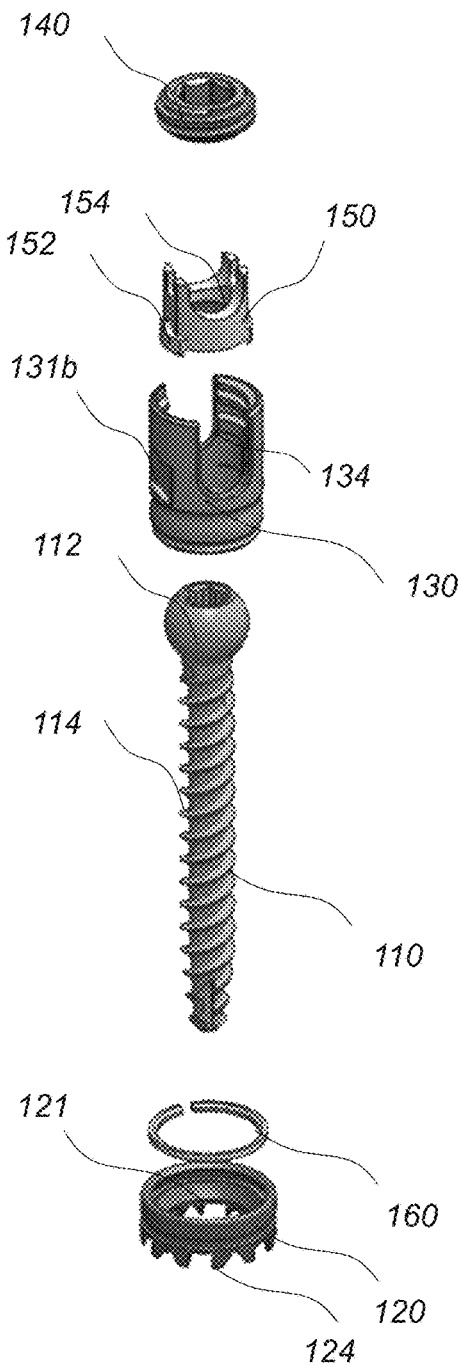
FIG. 5A depicts a fully exploded view of the spinal fixation assembly of FIG. 3A.
Figure 5B:
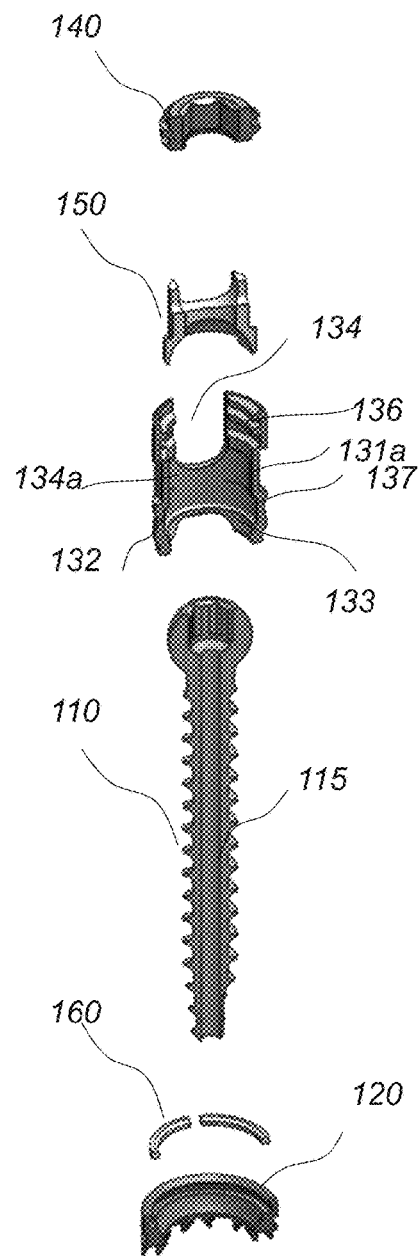
FIG. 5B depicts a cross-sectional view of the fully exploded spinal fixation assembly of FIG. 5A.
Figure 6A:
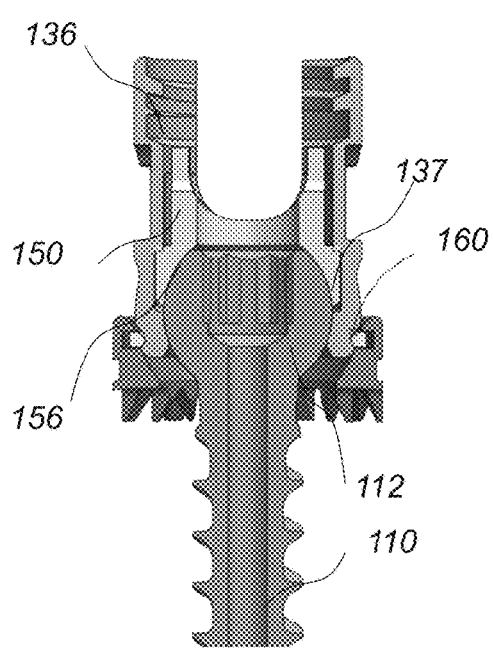
FIG. 6A depicts a side cross-sectional view of the upper portion of the spinal fixation assembly of FIG. 3A.
Figure 6B:
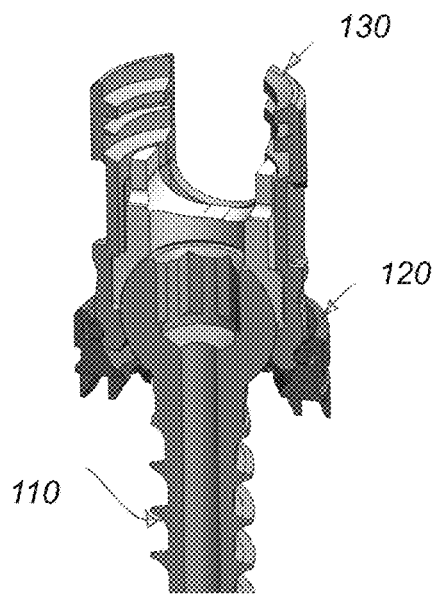
FIG. 6B depicts a perspective cross-sectional view of the upper portion of the spinal fixation assembly of FIG. 3A.
Figure 7A:
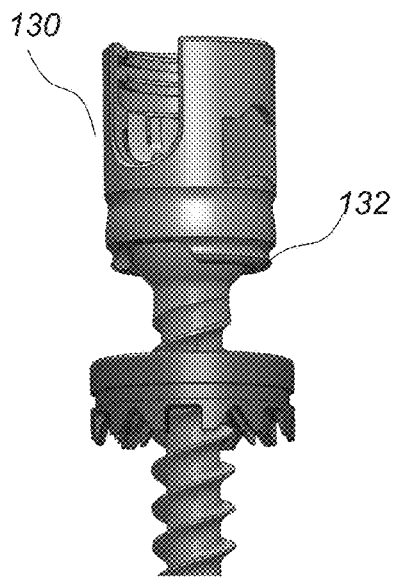
FIG. 7A depicts a side view of the upper portion of the spinal fixation assembly of FIG. 3A.
Figure 7B:
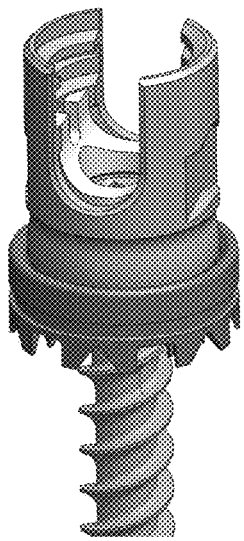
FIG. 7B depicts a perspective view of the upper portion of the spinal fixation assembly of FIG. 3A.

Referring to FIG. 2A and FIG. 2B, a spinal fixation system 90 according to this invention includes spinal fixation elements 100a-100e and 100a'-100e', and rods 95a and 95b. Spinal fixation elements 100a-100e and 100a'-100e' connect the facets of adjacent vertebras and are anchored along trajectories that lead into the vertebral body of one of the adjacent vertebras. In one example, fixation element 100b passes through and connects the inferior facets of L4 vertebra to the superior facets of the adjacent L5 vertebra and is anchored into the vertebral body of the L5 vertebra along trajectory 92. As shown in FIG. 2A and FIG. 2B, six adjacent vertebras L1, L2, L3, L4, L5, and S1 are connected via five fixation elements 100a-100e and 100a'-100e' and rods 95a, 95b on each of the left and right sides, respectively, whereas in prior art trans-pedicular rod fixation systems, the six adjacent vertebras would have required six fixation elements and a rod on each of the left and right sides.

Referring to FIG. 3A-FIG. 7B, spinal fixation assembly 100 includes a bone screw 110, a washer 120, a tulip-shaped seat 130, a rod seat 150, and a cap 140. Bone screw 110 is a cannulated screw and includes a spherical head 112 and a threaded elongated body 114. An elongated through opening 115 extends through the center of the spherical head 112 and through the center of the elongated body 114. The tulip-shaped seat 130 includes a bottom portion 132 that has a through-opening 133 and is shaped and dimensioned to receive the bone screw 110 so that the bottom portion 132 engages the head 112 of the bone screw 110 and prevents the bone screw 110 from passing entirely through. The tulip-shaped seat 130 also includes a side portion 134 that is shaped and dimensioned to receive the rod seat 150, rod 95, and cap 140. The inner surface 134a of the side portion includes upper threads 136 and a lower groove 137. Rod seat 150 has a cylindrically shaped hollow body that includes a circular protrusion 152 around the periphery of the lower outer surface, a semispherical bottom opening 156, and a semi-circular cut-out 154 through the top side portion. Circular protrusion 152 is dimensioned to engage groove 137 of the tulip-shaped seat 130, the semi-circular cut-out 154 through the top side portion is shaped and dimensioned to receive the rod 95, and the semispherical bottom opening 156 is shaped and dimensioned to engage the spherical head 112 of the bone screw 110. Rod seat 150 seats within the tulip-shaped seat 130 between the screw head 112 and the rod 95. In this embodiment, rod seat 150 is rotatably engageable with the inner side surface 134a of the tulip-shaped seat 130. In other embodiments, rod seat 150 is slidably engageable, and/or snappably engageable with the inner surface 134a of the tulip-shaped seat 130.

Washer 120 is a ring-shaped washer and has a through-opening 121, and teeth 124 extending from a bottom surface. The upper inner surface of washer 120 includes a groove 122 that is dimensioned and shaped to receive a snap-ring 160. Cap 140 is ring shaped and has outer threads that are shaped and dimensioned to engage the inner threads 136 on the top portion of the tulip shaped seat 130.

In operation, bone screw 110 passes through the through-opening 133 of the bottom of the seat 130 and through the through-opening 121 of the washer 120 and is driven into the inferior facets of a first vertebra, the superior facets of an adjacent second vertebra that are in contact with the inferior facets of the first vertebra and along a selected trajectory that leads into the vertebral body of the second vertebra. As the bone screw is being driven and secured into the vertebral body along the selected trajectory, the washer 120 adjusts its orientation and position to contour the local shape and anatomy of the vertebral body and is affixed onto the inferior facets of the first vertebra by inserting the washer teeth 124 into the facet bone. Next, rod 95 is inserted into the semi-circular cut-out 154 of the rod seat 150 and the orientation of rod 95 is adjusted. Once the desired orientation of rod 95 is selected, the position of rod 95 is secured into the rod seat 150 by threading cap 140 into the upper threads 136 of the seat 130. The position of the tulip-shaped seat 130 and of the rod seat 150 is secured relative to the bone screw orientation by snapping the bottom 133 of the seat 130 into the top of washer 120. Snap-ring 160 retains the tulip-shaped seat 130 and the washer 120 together.

The spinal fixation assembly 100 allows for multi-axial positioning of the bone screw 110 and multi-axial positioning of the tulip-shaped seat 130 and the supported rod 95. The spinal fixation assembly allows customization of the washer 120, bone screw 110, and rod 95. In one example, bone screws 110 having a length in the range of 20 mm to 80 mm are used. The components of the spinal fixation assembly 110 are made of bio-compatible materials including titanium, titanium alloys (e.g. titanium/aluminum/vanadium (Ti/Al/V) alloys), cobalt-chromium alloys, stainless steel, ceramics (alumina ceramic, zirconia ceramic, yttria zirconia ceramic, etc.), high strength polymers (e.g. PEEK, PEKK, etc.), pyrolytic carbon, tantalum, carbon composite materials, and combinations thereof, among others. Some materials are more appropriate for fixation surfaces, such as cobalt-chromium alloys, titanium, and (Ti/Al/V) alloys, but any material known in the art for use with fixation surfaces can be used in the present invention While one of skill in the art will recognize that fixation devices other than a bone screw 110 can be used without departing from the scope of the present invention, a bone screw is shown and described herein to illustrate the engagement of the fixation device 110 and the seat 130, as well as the method for locking the relative positions of the bone screw 110 and the rod 95. In one example, the height of seat 130 may range from about 0.25 inch to about 6 inches. In another example, the height of the seat 130 ranges from about 0.4 inch to about 0.45 inch. Also, the width of seat 130 may range from about 0.25 inch to about 1 inch. In another example, the width of the seat 130 ranges from about 0.39 inch to about 0.42 inch.

It will be understood by those skilled in the art that a tool can be used to cause the seat 130 to engage the washer 120. For example, the tool may engage the side grooves 131a, 131b on the outer side surface of the seat 130, and then be used to rotate or push the seat 130 into engagement with the washer 120.

Figure 8:
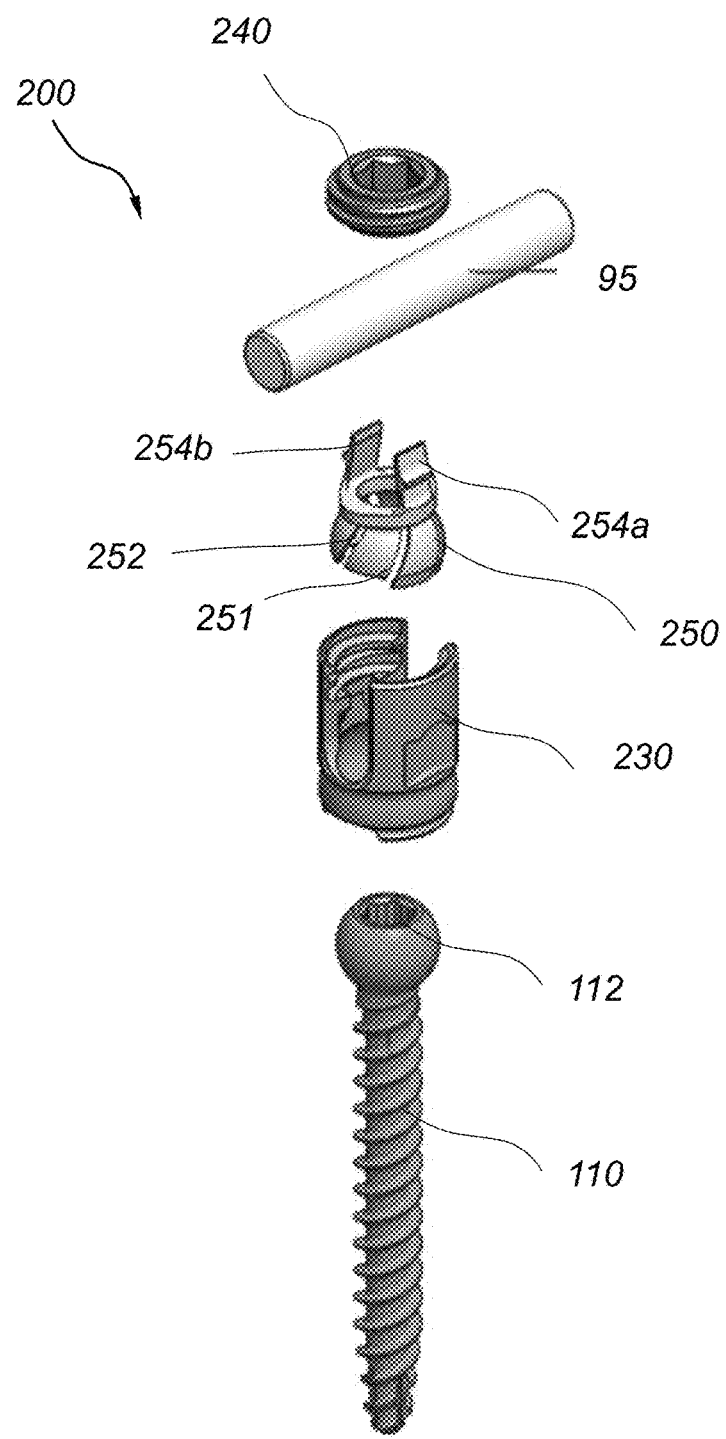
FIG. 8 depicts an exploded view of another embodiment of a trans-facet spinal fixation assembly according to this invention.

Referring to FIG. 8-FIG. 9C, in another embodiment, spinal fixation assembly 200 includes a bone screw 110, a tulip-shaped seat 230, a rod seat 250, and a cap 240. Bone screw 110 is a cannulated screw and includes a spherical head 112 and a threaded elongated body 114. An elongated through opening 115 extends through the center of the spherical head 112 and through the center of the elongated body 114. The tulip-shaped seat 130 includes a bottom portion 232 that has a through-opening 233 and is shaped and dimensioned to receive the bone screw 110 so that the bottom portion 232 engages the head 112 of the bone screw 110 and prevents the bone screw 110 from passing entirely through. The tulip-shaped seat 230 also includes a side portion 234 that is shaped and dimensioned to receive the rod seat 250, rod 95, and cap 240. The inner surface 234a of the side portion includes upper threads 236 and a lower groove 237. Rod seat 250 has a semi-spherical hollow lower portion 252 and two upward extending tabs 254a, 254b.

Lower portion 252 includes flexible segments 251 that are configured to surround the spherical head 112 of the bone screw 110. The upward extending tabs 254a, 254b are arranged opposite to each other and are dimensioned to receive rod 95 inbetween them. In this embodiment, bone screw 110 is driven into the vertebral body and the tulip-shaped seat 230 snaps onto the spherical head 112 of the screw 110 after the bone screw is in place. Segments 251 of the lower portion 252 of the rod seat extend outward to slide over the screw head 112 and then snap close to secure the seat 230 onto the bone screw head 112.

Figure 10A:
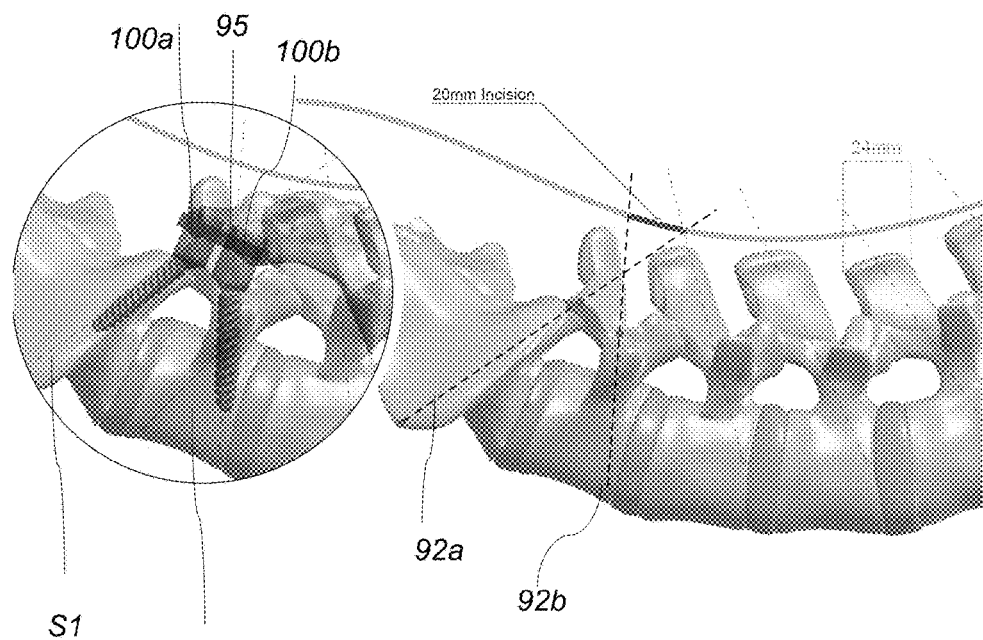
FIG. 10A and FIG. 10B depict side views of a one-level spinal fixation with a trans-facet fixation assembly according to this invention and a trans-pedicle fixation assembly.
Figure 10B:
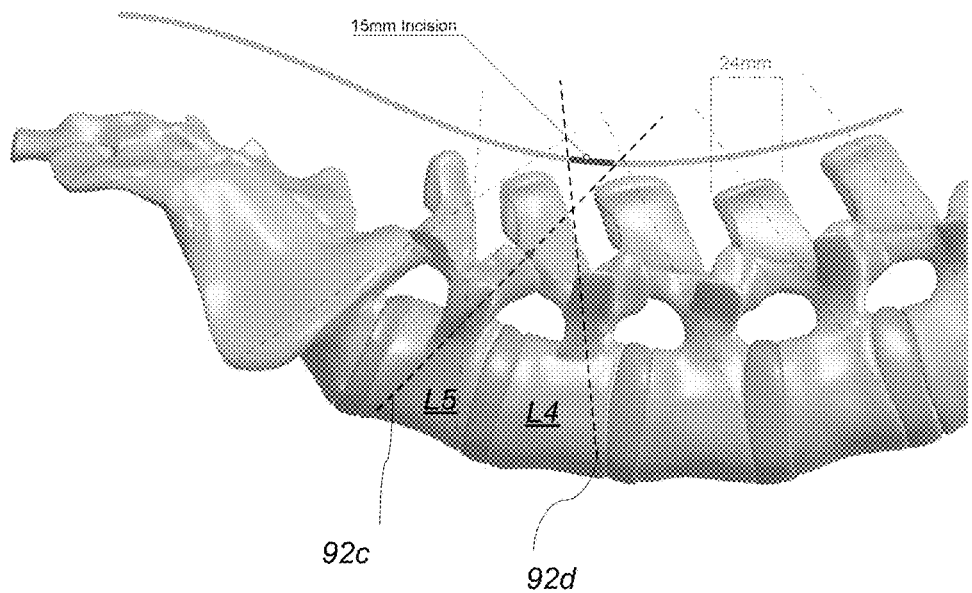

The spinal fixation assemblies 100, 200 are used in conjunction with one or more midline pedicle screws. Referring to FIG. 10A, in one example, a 20 mm incision is performed in the back of a patient and two spinal fixation assemblies 100a, 100b are inserted along trajectories 92a, 92b, respectively. Trajectory 92a is a trans-facet trajectory and trajectory 92b is a trans-pedicle trajectory. Spinal fixation assembly 100a is a trans-facet fixation assembly according to this invention and spinal fixation assembly 100b is a traditional trans-pedicle screw assembly. Spinal fixation assembly 100a connects the superior facet of S1 vertebra to the inferior facet of L5. Spinal fixation assembly 100b is anchored into the pedicle of L5. Rod 95 is secured between the two spinal fixation assemblies for achieving a single level S1-L5 stabilization. This spinal fixation arrangement uses the same number of fixation assemblies as in the traditional pedicle screw fixation arrangement. However, the use of the trans-facet spinal fixation assembly 100a reduces the incision size. FIG. 10B depicts another example of a single level L5-L4 stabilization by inserting fixations assemblies 100a, 100b, along trajectories 92c, 92d, respectively.

Figure 11A:
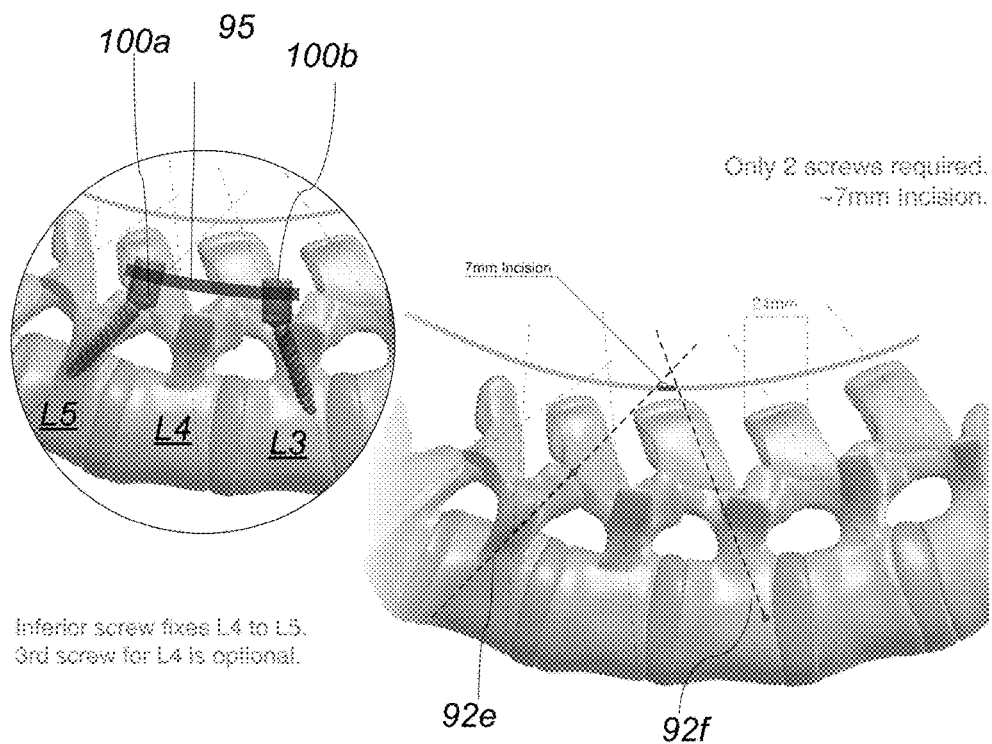
FIG. 11A depicts a side view of a two-level spinal fixation with a trans-facet fixation assembly according to this invention and a trans-pedicle fixation assembly.

In another example, only two spinal fixation assemblies are used to achieve a two-level stabilization. Referring to FIG. 11A, a 7 mm incision is performed in the back of a patient and two spinal fixation assemblies 100a, 100b are inserted along trajectories 92e, 92f, respectively. Spinal fixation assembly 100a is a trans-facet fixation assembly according to this invention and spinal fixation assembly 100b is a traditional trans-pedicle screw assembly. Spinal fixation assembly 100a connects the superior facet of L5 vertebra to the inferior facet of L4. Spinal fixation assembly 100b is anchored into the pedicle of L3 and rod 95 is secured between the two spinal fixation assemblies for achieving a two-level L5-L3 stabilization. Optionally, a third pedicle screw (not shown) is anchored into the pedicle of L4 vertebra. This spinal fixation arrangement reduces the incision size and the number of fixation screws from 8 screws to 4 screws bilaterally.

Figure 11B:
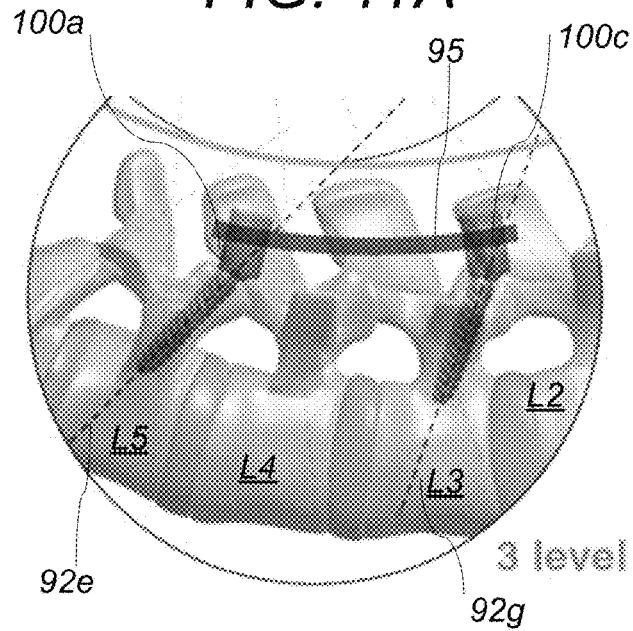
FIG. 11B depicts a side view of a three-level spinal fixation with two trans-facet fixation assemblies according to this invention.
Figure 12A:
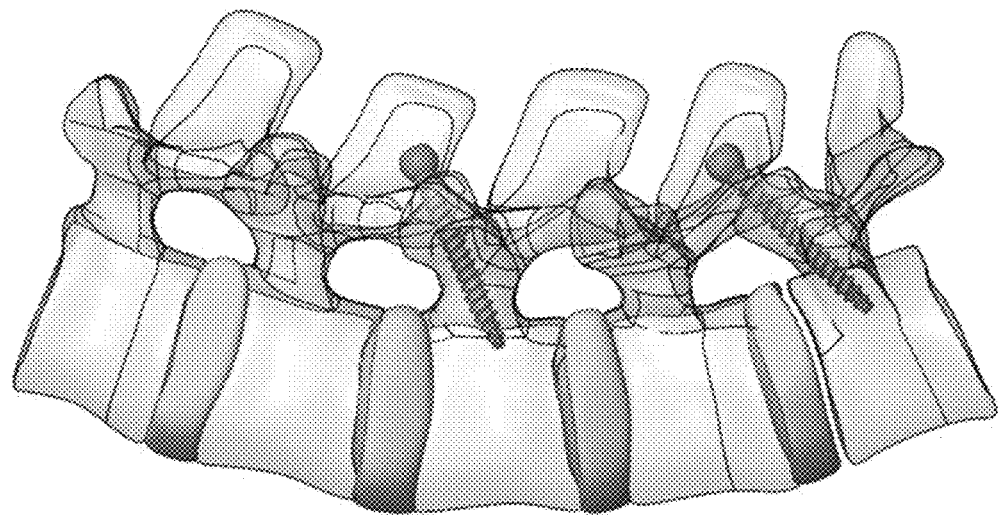
FIG. 12A depicts a side view of the trajectories for the three-level spinal fixation of FIG. 11B.
Figure 12B:
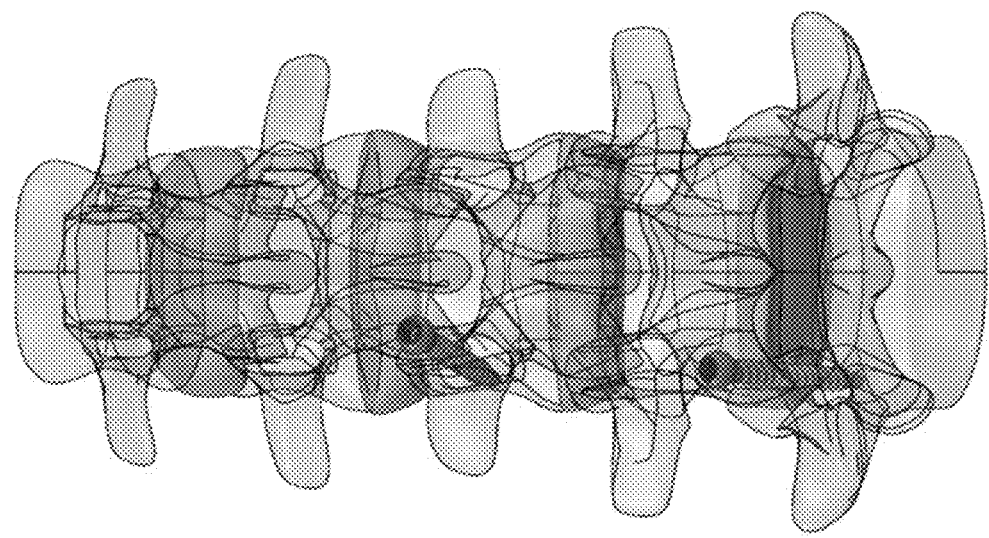
FIG. 12B depicts a posterior view the trajectories for the three-level spinal fixation of FIG. 11B.
Figure 13A:
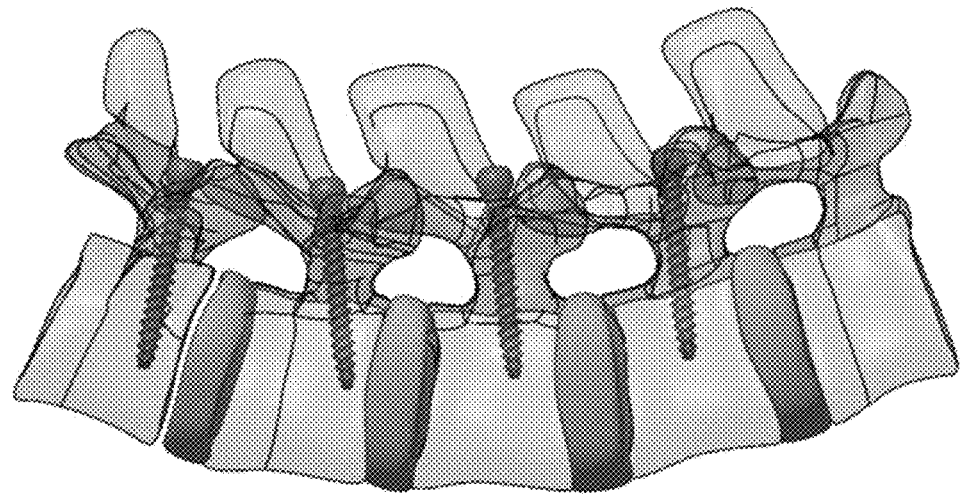
FIG. 13A depicts a side view of the trajectories for a three-level spinal fixation with four pedicle screw fixation assemblies.
Figure 13B:
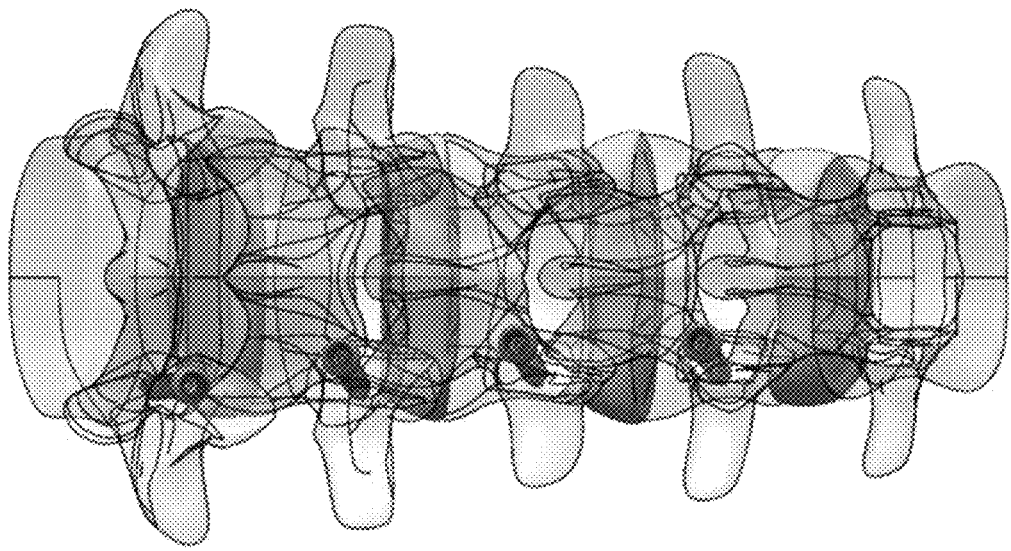
FIG. 13B depicts a posterior view of the trajectories for the three-level spinal fixation with four pedicle screw fixation assemblies of FIG. 13A.

In yet another example, only two spinal fixation assemblies are used to achieve a three-level stabilization. Referring to FIG. 11B, an incision is performed in the back of a patient and two spinal fixation assemblies 100a, 100c are inserted along trajectories 92e, 92g, respectively. Trajectories 92e, 92g are trans-facet, and spinal fixation assemblies 100a, 100c are both trans-facet assemblies according to this invention. Spinal fixation assembly 100a connects the superior facet of L5 vertebra to the inferior facet of L4. Spinal fixation assembly 100c connects the superior facet of L3 to the inferior facet of L2. Rod 95 is secured between the two spinal fixation assemblies for achieving a three-level L5-L2 stabilization. FIG. 12A is a side view of the spinal fixation trajectories and FIG. 12B is a posterior view of the of the spinal fixation trajectories for the three-level stabilization with the two trans-facet spinal fixation assemblies of this invention. In comparison, FIG. 13A is a side view of the spinal fixation trajectories and FIG. 13B is a posterior view of the of the spinal fixation trajectories for a three-level stabilization with the traditional pedicle screw fixation assemblies. As shown, the traditional pedicle screw stabilization arrangement requires four pedicle screws and a larger incision for inserting the pedicle screws and rod.

Several embodiments of the present invention have been described. Nevertheless, it will be understood that various modifications may be made without departing from the spirit and scope of the invention. Accordingly, other embodiments are within the scope of the following claims.

What is claimed is:

1. A spinal fixation device comprising:
a bone screw, a tulip-shaped seat, a rod seat, and a washer;
wherein the bone screw comprises a spherical head and a threaded elongated body extending along a first direction;
wherein the tulip-shaped seat comprises a bottom portion that has a through-opening shaped and dimensioned to receive the bone screw so that an inner surface of the bottom portion engages the spherical head of the bone screw and prevents the bone screw from passing entirely through the through-opening, while the spherical head remains polyaxially rotatable within the bottom portion of the tulip-shaped seat;
wherein the rod seat sits within and engages the inner surface of the tulip-shaped seat and wherein the rod seat comprises a semispherical bottom that is shaped and dimensioned to engage the spherical head of the bone screw while the spherical head remains polyaxially rotatable within the bottom portion of the tulip-shaped seat;
wherein the washer is ring-shaped and comprises a through-opening shaped and dimensioned to receive the threaded elongated body of the bone screw and an upper portion shaped and dimensioned to snappably-engage an outer surface of the tulip-shaped seat via a snap-ring.

2. The device of claim 1, wherein the rod seat further comprises a top portion with a semi-circular horizontal cut-out and is shaped and dimensioned to receive a rod extending along a second direction.

3. The device of claim 2, wherein the rod seat rotationally engages the inner surface of the tulip-shaped seat and further comprises a circular protrusion around a portion of an outer surface and wherein the circular protrusion engages a groove formed on the inner surface of the tulip-shaped seat and locks the position of the rod seat within the tulip-shaped seat so that the semi-circular horizontal cut-out of the rod seat is aligned with a semi-circular cut-out of the tulip-shaped seat.

4. The device of claim 1, further comprising a cap shaped and dimensioned to engage inner threads formed on an inner surface of a top portion of the tulip-shaped seat and to secure a rod within the rod seat.

5. The device of claim 1, wherein an inner surface of the top portion of the washer comprises a groove that is dimensioned to receive the snap-ring and to snappably-engage and secure the washer onto the outer surface of the tulip-shaped seat.

6. The device of claim 1, wherein the washer further comprises protrusions extending downward from a bottom portion of the washer.

7. The device of claim 1, wherein the spherical head of the bone screw comprises a hexagonal top opening and wherein the hexagonal top opening extends into a cylindrical opening of the elongated body of the bone screw and wherein the cylindrical opening extends along the first direction from the elongated body's top end to its bottom end.

8. The device of claim 1, wherein the spinal fixation element passes through and connects opposing facets of two adjacent vertebras and is anchored along a trajectory that leads into a vertebral body of one of the adjacent vertebras.

9. A spinal fixation device comprising:
a bone screw, a tulip-shaped seat, and rod seat;
wherein the bone screw comprises a spherical head and a threaded elongated body extending along a first direction;
wherein the tulip-shaped seat comprises a through-opening shaped and dimensioned to receive the rod seat;
wherein the rod seat sits within and snappably engages an inner surface of the tulip-shaped seat and wherein the rod seat comprises a semispherical bottom that is shaped and dimensioned to snappably engage the spherical head of the bone screw; and
wherein the rod seat comprises two upward extending tabs that are dimensioned to receive a rod extending along a second direction and wherein the bottom of the rod seat comprises flexible segments that snappably engage the spherical head of the bone screw.

10. A trans-facet spinal fixation system comprising:
first trans-facet spinal fixation element passing through and connecting a superior facet of a first vertebra to an opposing inferior facet of an adjacent second vertebra and being anchored along a trajectory that leads into a vertebral body of the first vertebra;
second trans-facet spinal fixation element passing through and connecting a superior facet of a third vertebra to an opposing inferior facet of an adjacent fourth vertebra and being anchored along a trajectory that leads into a vertebral body of the third vertebra; and
a rod supported onto the first and second trans-facet spinal fixation elements;
wherein the first trans-facet spinal fixation elements comprises a bone screw, a tulip-shaped seat, a rod seat, and a washer, and wherein the bone screw comprises a spherical head and a threaded elongated body, wherein the tulip-shaped seat comprises a bottom portion that has a through-opening shaped and dimensioned to receive the bone screw so that an inner surface of the bottom portion engages the spherical head of the bone screw and prevents the bone screw from passing entirely through the through-opening, while the spherical head remains polyaxially rotatable within the bottom portion of the tulip-shaped seat, wherein the rod seat sits within and engages the inner surface of the tulip-shaped seat and wherein the rod seat comprises a semispherical bottom that is shaped and dimensioned to engage the spherical head of the bone screw while the spherical head remains polyaxially rotatable within the bottom portion of the tulip-shaped seat, wherein the rod seat further comprises a to portion with a semi-circular horizontal cut-out and is shaped and dimensioned to receive the rod, and wherein the washer is ring-shaped and comprises a through-opening shaped and dimensioned to receive the threaded elongated body of the bone screw and an upper portion shaped and dimensioned to snappably-engage an outer surface of the tulip-shaped seat, and wherein the rod seat comprises two upward extending tabs that are dimensioned to receive a rod extending along a second direction and wherein the bottom of the rod seat comprises flexible segments that snappably engage the spherical head of the bone screw.

11. The system of claim 10, wherein the second trans-facet spinal fixation elements comprises a bone screw, a tulip-shaped seat, and a rod seat and wherein the bone screw comprises a spherical head and a threaded elongated body extending along a first direction, wherein the tulip-shaped seat comprises a through-opening shaped and dimensioned to receive the rod seat, and wherein the rod seat sits within and snappably engages an inner surface of the tulip-shaped seat and wherein the rod seat comprises a semispherical bottom that is shaped and dimensioned to snappably engage the spherical head of the bone screw via a snap-ring.

12. A spinal fixation system comprising:
a trans-facet spinal fixation element passing through and connecting a superior facet of a first vertebra to an opposing inferior facet of an adjacent second vertebra and being anchored along a trajectory that leads into a vertebral body of the first vertebra;
a trans-pedicle spinal fixation element being anchored into a pedicle of a third vertebra; and
a rod supported onto the trans-facet spinal fixation element and the trans-pedicle spinal fixation element; and
wherein the trans-facet spinal fixation element comprises a bone screw, tulip-shaped seat, and a rod seat and wherein the bone screw comprises a spherical head and a threaded elongated body extending along a first direction, wherein the tulip-shaped seat comprises a through-opening shaped and dimensioned to receive the rod seat, and wherein the rod seat sits within and snappably engages an inner surface of the tulip-shaped seat and wherein the rod seat comprises a semispherical bottom that is shaped and dimensioned to snappably engage the spherical head of the bone screw via a snap-ring.

13. A trans-facet spinal fixation method comprising:
inserting a first trans-facet spinal fixation element through a superior facet of a first vertebra, and through an opposing inferior facet of an adjacent second vertebra and anchoring the first trans-facet spinal fixation element along a trajectory that leads into a vertebral body of the first vertebra;
inserting a second trans-facet spinal fixation element through a superior facet of a third vertebra, and through an opposing inferior facet of an adjacent fourth vertebra and anchoring the second trans-facet spinal fixation element along a trajectory that leads into a vertebral body of the third vertebra; and
inserting and supporting a rod onto the first and second trans-facet spinal fixation elements; and
wherein the first trans-facet spinal fixation elements comprises a bone screw, a tulip-shaped seat, a rod seat, and a washer, and wherein the bone screw comprises a spherical head and a threaded elongated body, wherein the tulip-shaped seat comprises a bottom portion that has a through-opening shaped and dimensioned to receive the bone screw so that an inner surface of the bottom portion engages the spherical head of the bone screw and prevents the bone screw from passing entirely through the through-opening, while the spherical head remains polyaxially rotatable within the bottom portion of the tulip-shaped seat, wherein the rod seat sits within and engages the inner surface the tulip-shaped seat and wherein the rod seat comprises a semispherical bottom that is shaped and dimensioned to engage the spherical head of the bone screw while the spherical head remains polyaxially rotatable within the bottom portion of the tulip-shaped seat, wherein the rod seat further comprises a top portion with a semi-circular horizontal cut-out and is shaped and dimensioned to receive the rod and wherein the washer is ring-shaped and comprises a through-opening shaped and dimensioned to receive the threaded elongated body of the bone screw an upper portion-shaped and dimensioned to snappably-engage an outer surface of the tulip-shaped seat, and wherein the rod seat comprises two upward extending tabs that are dimensioned to receive the rod and wherein the bottom of the rod seat comprises flexible segments that snappably engage the spherical head of the bone screw.

14. The method of claim 13, wherein the second trans-facet spinal fixation elements comprises a bone screw, a tulip-shaped seat, and a rod seat and wherein the bone screw comprises a spherical head and a threaded elongated body extending along a first direction, wherein the tulip-shaped seat comprises a through-opening shaped and dimensioned to receive the rod seat, and wherein the rod seat sits within and snappably engages an inner surface of the tulip-shaped seat and wherein the rod seat comprises a semispherical bottom that is shaped and dimensioned to snappably engage the spherical head of the bone screw via a snap-ring.

* * * * *